United States Patent [19]
Ishii et al.

[11] Patent Number: 6,037,477
[45] Date of Patent: Mar. 14, 2000

[54] OXIDATION PROCESS OF ETHERS

[75] Inventors: Yasutaka Ishii, 19-21, Besshohonmachi, Takatsuki-shi, Osaka 569-1112; Tatsuya Nakano, Himeji, both of Japan

[73] Assignees: Daicel Chemical Industries, Ltd.; Yasutaka Ishii, both of Osaka, Japan

[21] Appl. No.: 09/074,604

[22] Filed: May 8, 1998

[30] Foreign Application Priority Data

May 13, 1997 [JP] Japan ..................................... 9-122526

[51] Int. Cl.$^7$ ................. C07D 207/404; C07D 207/448; C07D 487/06; C07D 207/444
[52] U.S. Cl. .......................... 548/545; 548/548; 548/549; 548/453
[58] Field of Search ..................... 548/545, 548, 548/549

[56] References Cited

FOREIGN PATENT DOCUMENTS

0824962A1  2/1998  European Pat. Off. .
838909    2/1996  Japan .

OTHER PUBLICATIONS

Ishii et al., *J. Org. Chem.*, vol. 61, pp. 4520–4526 (1996).
Yoshino et al., *J. Org. Chem.*, vol. 62, No. 20, pp. 6810–6813 (Oct. 1997).
Takeno et al., Aerobic Oxidation by Using N–hydroxyphthalimide, 67th Spring Annual Meeting of Chemical Society of Japan, Lecture Draft II, Dec. 1994.

*Primary Examiner*—Johann Richter
*Assistant Examiner*—Dominic Keating
*Attorney, Agent, or Firm*—Birch, Stewart, Kolasch & Birch, LLP

[57] ABSTRACT

An ether is oxidized with oxygen under an oxidation catalyst comprising an imide compound (such as N-hydroxyphthalimide) or the imide compound and a co-catalyst to produce the corresponding chain or cyclic ester or anhydride. The co-catalyst may be a transition metal compound. The above process provides a process for oxidizing an ether by oxygen efficiently to produce the corresponding oxide (such as an ester, an hydride) with high conversion and selectivity.

10 Claims, No Drawings

OXIDATION PROCESS OF ETHERS

FIELD OF THE INVENTION

This invention relates to a useful oxidation process for producing a corresponding oxide (such as a chain or cyclic ester, an acid anhydride) from an ether.

BACKGROUND OF THE INVENTION

A chain or cyclic ester and an acid anhydride are important compounds as an intermediate of a medicine, a perfume and a dye, a intermediate in organic synthesis, and a raw material of a polymer resin.

A chain ester may be produced by esterification of a carboxylic acid and an alcohol. A lactone may be produced by rearrangement reaction of a cyclic ketone by a peracid.

Japanese Patent Application Laid-open No. 38909/1996 (JP-A-8-38909) proposes a process for producing an adipic acid by oxidizing cyclohexanone or cyclohexanol with molecular oxygen in the presence of an oxidation catalyst comprising an imide compound. A process for generating isocoumarin by oxidizing-isochroman with molecular oxygen in the presence of the oxidation catalyst comprising the imide compound is also proposed.

However, a process for producing a corresponding ester or acid anhydride from a chain or cyclic ether by an oxidation with oxygen has been unknown.

SUMMARY OF THE INVENTION

It is, therefore, an object of the present invention to provide a useful process for oxidizing an ether with oxygen efficiently to produce an ester or an acid anhydride.

It is another object of the present invention to provide a process for producing an ester or an acid anhydride from an ether by oxygen under a mild or moderate condition with high conversion and selectivity.

The inventors of the present invention did intensive investigation to accomplish the above objects, and as a result, found that an oxide corresponding to an ether may be directly and efficiently produced with a high conversion and selectivity from the ether using an oxidation catalyst comprising (i) N-hydroxyphthalimide compound or (ii) N-hydroxyphthalimide compound and a co-catalyst.

Thus, the process of the present invention comprises oxidizing an ether by contacting the ether with oxygen in the presence of an oxidation catalyst comprising an imide compound shown by the following formula (1),

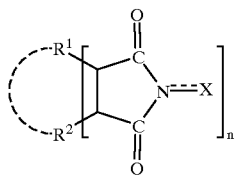

(1)

wherein $R^1$ and $R^2$ respectively represent a hydrogen atom, a halogen atom, an alkyl group, an aryl group, a cycloalkyl group, a hydroxyl group, an alkoxy group, a carboxyl group, an alkoxycarbonyl group, or an acyl group; or $R^1$ and $R^2$ may bond together to form a double bond, or an aromatic or non-aromatic ring; X represents an oxygen atom or a hydroxyl group; and n denotes an integer of 1 to 3. The oxidation-catalyst may comprise the imide compound shown by the formula (1) and a co-catalyst. The co-catalyst may comprise a transition metal compound (such as an oxide, an organic acid salt, a inorganic acid salt, a halide, a complex, and heteropolyacid or salt thereof)

In the process of the present invention, an ester or an anhydride may be produced by contacting an ether with oxygen in the presence of the above catalyst.

In the specification, "an ether" simply refers to "a substrate". "An ether" includes not only a chain ether but also a cyclic ether, and a compound having not only single ether bond but plural ether bonds.

DETAILED DESCRIPTION OF THE INVENTION

Imide Compound In the compound shown by the formula (1), the halogen atom, as the substituents $R^1$ and $R^2$, includes iodine, bromine, chlorine and fluorine atoms. The alkyl group includes, for example, methyl, ethyl, propyl, isopropyl, butyl, isobutyl, sec-butyl, t-butyl, pentyl, hexyl, heptyl, octyl, decyl, or other straight chain or branched chain alkyl groups each having about 1 to 10 carbon atoms. An illustrative preferred alkyl group includes alkyl groups having about 1 to 6 carbon atoms, in particular alkyl groups having about 1 to 4 carbon atoms.

As the aryl group, there may be mentioned, for instance, a phenyl group and a naphthyl group. Examples of the cycloalkyl group include cyclopentyl, cyclohexyl, and cyclooctyl groups. The alkoxy group includes, for example, methoxy, ethoxy, propoxy, isopropoxy, butoxy, isobutoxy, t-butoxy, pentyloxy, hexyloxy, and other alkoxy groups each having about 1 to 10 carbon atoms. Among them, alkoxy groups having about 1 to 6 carbon atoms, in particular alkoxy groups having about 1 to 4 carbon atoms are preferable.

Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, and other alkoxycarbonyl groups each having about 1 to 10 carbon atoms in the alkoxy moiety. A preferred alkoxycarbonyl group includes those each having about 1 to 6 carbon atoms in the alkoxy moiety, among which alkoxycarbonyl groups each having about 1 to 4 carbon atoms in the alkoxy moiety are typically desirable.

The acyl group includes, for instance, formyl, acetyl, propionyl, butyryl, isobutyryl, valeryl, isovaleryl, pivaloyl, and other acyl groups each having about 1 to 6 carbon atoms.

The substituents $R^1$ and $R^2$ may be either the same or different from each other. In the formula (1), $R^1$ and $R^2$ may bond together to form a double bond, or an aromatic or non-aromatic ring. A preferred aromatic or non-aromatic ring may be a ring having about 5 to 12 members, in particular about 6 to 10 members. Such a ring may be a heterocyclic ring or a condensed heterocyclic ring, and it may practically be a hydrocarbon ring. As such a ring, there may be mentioned, for instance, non-aromatic alicyclic rings (e.g., cyclohexane ring and other cycloalkane rings which may have a substituent, cyclohexene ring and other optionally substituted cycloalkene rings), non-aromatic bridged (cross-linked) rings (e.g., 5-norbornene ring and other optionally substituted bridged hydrocarbon rings), benzene ring, naphthalene ring and other optionally substituted aromatic rings. The ring may practically comprise an aromatic ring.

A preferred imide compound includes compounds shown by the following formula,

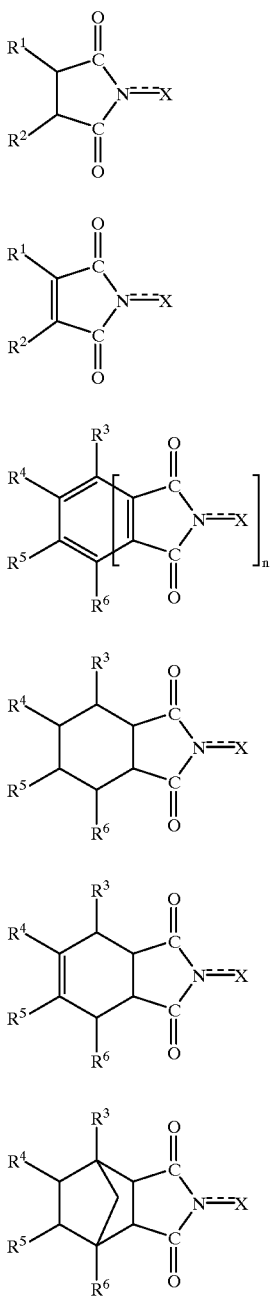

wherein $R^3$, $R^4$, $R^5$ and $R^6$ independently represent a hydrogen atom, an alkyl group, a hydroxyl group, an alkoxy group, a carboxyl group, an alkoxycarbonyl group, an acyl group, a nitro group, a cyano group, an amino group or a halogen atom; and $R^1$, $R^2$ and n have the same meanings as defined above.

In the substituents $R^3$, $R^4$, $R^5$ and $R^6$, the alkyl group includes alkyl groups similar to those exemplified above, in particular alkyl groups each having about 1 to 6 carbon atoms. The alkoxy group includes the same alkoxy groups as mentioned above, in particular alkoxy groups each having about 1 to 4 carbon atoms. Examples of the alkoxycarbonyl group include the same alkoxycarbonyl groups as exemplified above, in especial alkoxycarbonyl groups each having about 1 to 4 carbon atoms in the alkoxy moiety. As the acyl group, there may be mentioned the similar acyl groups to those mentioned above, in particular acyl groups each having about 1 to 6 carbon atoms. Examples of the halogen atom include fluorine, chlorine and bromine atoms. The substituents $R^3$, $R^4$, $R^5$ and $R^6$ may practically be hydrogen atoms, lower alkyl groups each having 1 to 4 carbon atoms, carboxyl groups, nitro groups or halogen atoms, respectively.

The symbol X in the formula (1) denotes an oxygen atom or a hydroxyl group, and n usually denotes about 1 to 3, preferably 1 or 2. The imide compound shown by the formula (1) can be used singly or in combination in the oxidation reaction.

As examples of the acid anhydride corresponding to the imide compound of the formula (1), there may be mentioned succinic anhydride, maleic anhydride, or other saturated or unsaturated aliphatic dicarboxylic acid anhydrides, tetrahydrophthalic anhydride, hexahydrophthalic anhydride (1,2-cyclohexanedicarboxylic acid anhydride), 1,2,3,4-cyclohexanetetracarboxylic acid 1,2-anhydride, and other saturated or unsaturated nonaromatic cyclic polycarboxylic acid anhydrides (alicyclic polycarboxylic acid anhydrides), hetic anhydride, himic anhydride, and other bridged cyclic polycarboxylic acid anhydrides (alicyclic polycarboxylic acid anhydrides), phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8;4,5-naphthalenetetracarboxylic acid dianhydride, and other aromatic polycarboxylic acid anhydrides.

Examples of a preferred imide compound include N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide, N-hydroxytrimellitimide, N,N'-dihydroxypyromellitimide, N,N'-dihydroxynaphthalenetetracarboximide and so forth. A typically preferable imide compound includes an N-hydroxyimide compound derived from an alicyclic polycarboxylic acid anhydride, in particular from an aromatic polycarboxylic acid anhydride, such as N-hydroxyphthalimide.

The imide compound may be prepared by a conventional imidation process (a process for the formation of an imide), such as a process that comprises the steps of allowing a corresponding acid anhydride to react with hydroxylamine $NH_2OH$ for ring-opening of an acid anhydride group, and closing the ring to form the imide.

Co-catalyst

A catalyst may comprise the imide compounds of the formula (1) and a co-catalyst. The co-catalyst includes or comprises metal compounds such as a compound comprising or containing a Group 2A element of the Periodic Table of Elements (e.g., magnesium, calcium, strontium, barium), a transition metal compound, or compounds containing a Group 3B element (e.g., boron B, aluminium Al) of the Periodic Table of Elements. These co-catalysts may be employed independently or in combination.

As the elements of the transition metal, there may be mentioned, for instance, Group 3A elements of the Periodic Table of Elements (e.g., scandium Sc, yttrium Y, and lanthanum La, cerium Ce, samarium Sm and other lanthanoid elements, actinium Ac and other actinoid elements), Group 4A elements of the Periodic Table of Elements (e.g., titanium Ti, zirconium Zr, hafnium Hf), Group 5A elements (e.g., vanadium V, niobium Nb, tantalum Ta), Group 6A elements (e.g., chromium Cr, molybdenum Mo, tungsten W), Group 7A elements (e.g., manganese Mn, technetium Tc, rhenium Re), Group 8 elements (e.g., iron Fe, ruthenium Ru, osmium Os, cobalt Co, rhodium Rh, iridium Ir, nickel Ni, palladium Pd, platinum Pt), Group 1B elements (e.g., copper Cu, silver Ag, gold Au) and Group 2A elements of the Periodic Table of Elements (e.g., zinc Zn, cadmium Cd).

A preferred element constituting the co-catalyst includes elements of the transition metals (such as lanthanoid elements (e.g., Ce), actinoid elements and other Group 3A elements of the Periodic Table of Elements, Ti, Zr and other Group 4A elements, V, Nb or other Group 5A elements, Cr, Mo, W and other Group 6A elements, Mn, Tc, Re or other Group 7A elements, Fe, Ru, Co, Rh, Ni and other Group 8 elements, or Cu and other Group 1B elements) and B and Group 3B elements. The oxidation number of the metal elements constituting the co-catalyst is not particularly limited, and may be, for example 0, +2, +3, +4, +5 and +6 according to the variety of elements. The divalent transition metal compounds (such as a divalent cobalt compound, a divalent manganese compound) may be practically used as the co-catalyst.

The species of the co-catalyst may be a simple substance or hydroxide of a metal. The co-catalyst may practically be an a metal oxide (comprising a double oxide or an oxygen acid salt) comprising the element, an organic acid salt comprising the element, an inorganic acid salt comprising the element, a halide comprising the element, a coordinate compound (a complex) comprising the metal element, or a polyacid (a heteropolyacid or an isopolyacid) comprising the element or a salt thereof.

As the boron compound, there may be mentioned, for example, a boron hydride (e.g., borane, diborane, tetraborane, pentaborane, decaborane), a boric acid (e.g., orthoboric acid, metaboric acid, tetraboric acid), a borate (e.g., a nickel borate, magnesium borate, manganese borate), $B_2O_3$, and other boron oxides, borazane, borazene, borazine, boron amide, boron imide, and other nitrogen-containing boron compounds, $BF_3$, $BCl_3$, tetrafluoroborate, and other halides, esters of boric acid (e.g., methyl borate, phenyl borate). A preferred boron compound includes boron hydrides and orthoboric acid and other boric acids or salts thereof, among which a boric acid may preferably be employed.

The hydroxide includes $Mn(OH)_2$, $MnO(OH)$, $Fe(OH)_2$ and $Fe(OH)_3$, typically speaking. Examples of the metallic oxide include $Sm_2O_3$, $TiO_2$, $ZrO_2$, $V_2O_3$, $V_2O_5$, CrO, $Cr_2O_3$, $MoO_3$, MnO, $Mn_3O_4$, $Mn_2O_3$, $MnO_2$, $Mn_2O_7$, FeO, $Fe_2O_3$, $Fe_3O_4$, $RuO_2$, $RuO_4$, CoO, $CoO_2$, $Co_2O_3$, $RhO_2$, $Rh_2O_3$, $Cu_2O_3$. As examples of the double oxide or oxygen acid salt, there may be mentioned $MnAl_2O_4$, $MnTiO_3$, $LaMnO_3$, $K_2Mn_2O_5$, $CaO.xMnO_2$ (x=0.5, 1, 2, 3, 5), manganese salts [e.g., $Na_3MnO_4$, $Ba_3(MnO_4)_2$ and other manganates(V), $K_2MnO_4$, $Na2MnO_4$, $BaMnO_4$ and other manganates(VI), $KMnO_4$, $NaMnO_4$, $LiMnO_4$, $NH_4MnO_4$, $CsMnO_4$, $AgMnO_4$, $Ca(MnO)_4)_2$, $Zn(MnO_4)_2$, $Ba(MnO_4)_2$, $Mg(MnO_4)_2$, $Cd(MnO_4)_2$ and other permanganates].

As the organic acid salts, there may be exemplified as cobalt acetate, manganese acetate, cobalt propionate, manganese propionate, cobalt naphthenate, manganese naphthenate, cobalt stearate, manganese stearate and other salts with a $C_{2-20}$ fatty acid, manganese thiocyanate, and corresponding salts of Ce, Ti, Zr, V, Cr, Mo, Fe, Ru, Ni, Pd, Cu and Zn. The inorganic acid salt includes, for instance, cobalt nitrate, iron nitrate, manganese nitrate, nickel nitrate, copper nitrate, and other nitrates, and sulfates, phosphates and carbonates each corresponding to these nitrates (e.g., cobalt sulfate, iron sulfate, manganese sulfate, cobalt phosphate, iron phosphate, manganese phosphate, an iron carbonate, a manganese carbonate, iron perchlorate). As the halides, there may be mentioned, for instance, $SmCl_3$, $SmCl_2$, $TiCl_2$, $ZrCl_2$, $ZrOCl_2$, $VCl_3$, $VOCl_2$, $MnCl_2$, $MnCl_3$, $FeCl_2$, $FeCl_3$, $RuCl_3$, $CoCl_2$, $RhCl_2$, $RhCl_3$, $NiCl_2$, $PdCl_2$, $PtCl_2$, CuCl, $CuCl_2$ and other chlorides, or fluorides, bromides or iodides each corresponding to these chlorides (e.g., $MnF_2$, $MnBr_2$, $MnF_3$, $FeF_2$, $FeF_3$, $FeBr_2$, $FeBr_3$, $FeI_2$, CuBr, $CuBr_2$) and other halides, $M^1MnCl_3$, $M^1{}_2MnCl_4$, $M^1{}_2MnCl_5$, $M^1{}_2MnCl_6$, wherein $M^1$ represents a monovalent metal, and other complex halides.

The ligand constituting the complex includes, for example, OH (hydroxo), methoxy, ethoxy, propoxy, butoxy and other alkoxy groups, acetyl (OAc), propionyl and other acyl groups, methoxycarbonyl (acetato), ethoxycarbonyl and other alkoxycarbonyl groups, acetylacetonato (AA), cyclopentadienyl group, chlorine, bromine and other halogen atoms, CO, CN, oxygen atom, $H_2O$ (aquo), phosphine (e.g., triphenylphosphine and other triarylphosphine) and other phosphorus compounds, $NH_3$ (ammine), NO, $NO_2$ (nitro), $NO_3$ (nitrato), ethylenediamine, diethylenetriamine, pyridine, phenanthroline and other nitrogen-containing compounds. In the complexes or complex salts, the same or different ligands may be coordinated singly or in combination. The preferable ligand includes, for example, OH, an alkoxy group, an acyl group, an alkoxycarbonyl group, acetylacetonato, a halogen atom, CO, CN, $H_2O$ (aquo), triphenylphosphine and other phosphorus compounds, and a nitrogen-containing compound inclusive of $NH_3$, $NO_2$ and $NO_3$.

A preferable complex includes the complexes containing the preferable transition metal element. The transition metal element and the ligand may optionally be employed in combination to form a complex. Such a complex includes, for instance, acetylacetonato complexes [e.g., acetylacetonato complex of Ce, Sm, Ti, Zr, V, Cr, Mo, Mn, Fe, Ru, Co, Ni, Cu and Zn, titanylacetylacetonato complex $TiO(AA)_2$, zirconylacetylacetonato complex $ZrO(AA)_2$, vanadylacetylacetonato complex $VO(AA)_2$], carbonyl complexes or cyclopentadienyl complexes [e.g., tricarbonylcyclopentadienylmanganese(I), biscyclopentadienylmanganese(II), biscyclopentadienyliron (II), $Fe(CO)_5$, $Fe_2(CO)_9$, $Fe_3(CO)_{12}$], nitrosyl compounds [e.g., $Fe(NO)_4$, $Fe(CO)_2(NO)_2$], thiocyanato complexes [e.g., thiocyanatocobalt, thiocyanatomanganese, thiocyanatoiron], or acetyl complexes [e.g. cobalt acetate, manganese acetate, iron acetate, copper acetate, zirconyl acetate $ZrO(OAc)_2$, titanyl acetate $TiO(OAc)_2$, vanadyl acetate $VO(OAc)_2$].

The polyacid is practically at least one member selected from Group 5 elements or Group 6 elements of the Periodic Table of Elements, such as V (vanadic acid), Mo (molybdic acid) or W (tungstic acid), typically speaking. There is no particular limit as to the central atom, and it may be any of, for instance, Be, B, Al, Si, Ge, Sn, Ti, Zr, Th, N, P, As, Sb, V, Nb, Ta, Cr, Mo, W, S, Se, Te, Mn, I, Fe, Co, Ni, Rh, Os, Ir, Pt or Cu. As illustrative examples of the heteropolyacid, there may be mentioned cobaltmolybdic acid, cobalttungstic acid, molybdenumtungstic acid, manganesemolybdic acid, manganesetungstic acid, manganesemolybdenumtungstic acid, vanadomolybdophosphoric acid, manganesevanadiummolybdic acid, manganesevanadomolybdophosphoric acid, vanadiummolybdic acid, vanadiumtungstic acid, silicomolybdic acid, silicotungstic acid, phosphomolybdic acid, phosphotangstic acid, phosphovanadomolybdic acid, and phosphovanadotangstic acid.

A catalyst comprising the imide compound shown by the formula (1) or the imide compound and the above co-catalyst may be whichever of a homogeneous system or a heterogeneous system. The catalyst may be a solid catalyst comprising a catalytic component supported on a support or carrier, as well. As the support, use can be practically made of active carbon, zeolite, silica, silica-alumina, bentonite, or other porous supports. In the solid catalyst, a supporting amount of the imide compound of the formula (1) may be about 0.1 to 50 parts by weight, preferably about 0.5 to 30 parts by weight and more preferably about 1 to 20 parts by weight relative to 100 parts by weight of the support. A ratio of the co-catalyst supported on the support is about 0.1 to 30 parts by weight, preferably about 0.5 to 25 parts by weight, and more preferably about 1 to 20 parts by weight, relative to 100 parts by weight of the support.

The amount of the imide compound of the formula (1) may be selected from a wide range and be, for example, about 0.001 (0.1 mole %) to 1 mole (100 mole %), preferably about 0.001 (0.1 mole %) to 0.5 mole (50 mole %), more preferably about 0.01 to 0.30 mole and practically about 0.01 to 0.25 mole, relative to 1 mole of ethers, typically speaking.

The amount of the co-catalyst (a co-oxidizing agent) can be liberally selected from a range not interfering with the reactivity and selectivity, and is, for example, about 0.0001 mole (0.1 mole %) to 1 mole (100 mole %), preferably about 0.0001 to 0.7 mole, and more preferably about 0.001 to 0.5 mole relative to one mole of ethers. The co-catalyst is practically used in a ratio of 0.0005 to 0.5 mole (e.g., about 0.005 to 0.5 mole) per one mole of ethers.

Incidentally, an increase of the amount of co-catalyst relative to the imide compound may deteriorate the activities of the imide compound. Therefore, for the purpose of maintaining high activities of the oxidation catalyst, the proportion of co-catalyst is not less than an effective amount to not more than about 0.1 mole (e.g., about 0.001 to 0.1 mole, preferably about 0.005 to 0.08 mole, and more preferably about 0.01 to 0.07 mole) relative to 1 mole of the imide compound.

When the heteropolyacid or a salt thereof may be used as a co-catalyst, the amount is about 0.1 to 25 parts by weight, preferably 0.5 to 10 parts by weight, and more preferably 1 to 5 parts by weight relative to 100 parts by weight of a substrate.

Such an oxidation catalyst has high oxidation activity and the use of the catalyst catalytically accelerates an oxidation reaction of ethers even in mild or moderate conditions. Thus, ethers may be efficiently oxidized with high selectivity and a corresponding oxide (e.g., esters, anhydrides) corresponding to an ether may be produced. Therefore, in the process of the present invention, an ether is contacted with oxygen to oxidize in the presence of the oxidation catalyst.

Substrate

The ether as a substrate may be whichever of a chain ether or a cyclic ether (a non-aromatic cyclic ether or an aromatic cyclic ether). The ethers may have plural ether bonds in the molecular.

Incidentally, a non-aromatic cyclic ether among cyclic ethers may be oxidized in the presence of the oxidation catalyst comprising the imide compound shown by formula (1). A non-aromatic cyclic ether and an aromatic cyclic ether may be oxidize the presence of the oxidation catalyst comprising the imide compound and the co-catalyst.

The chain ether (linear or non-cyclic ether) includes an ether shown by the following formula (2):

$$R^{7a}\text{—O—}R^{7b} \qquad (2)$$

wherein $R^{7a}$ and $R^{7b}$ are the same or different alkyl group or alkenyl group, and an ester shown by the following formula (3):

$$R^8\text{—O—}R^9 \qquad (3)$$

wherein $R^8$ represents an alkyl group or an alkenyl group, and $R^9$ represents a cycloalkyl group or an aryl group.

In ethers shown by the formula (2) and (3), the alkyl group may include, for example, a straight chain or branched chain $C_{1-5}$ alkyl group (e.g., methyl group, ethyl group, propyl group, isopropyl group, butyl group, isobutyl group, pentyl group, isopentyl group, hexyl group, heptyl group and octyl group), and preferably $C_{1-10}$ alkyl groups.

The alkenyl group may include, for example, a straight chain or branched chain $C_{2-15}$ alkenyl group [e.g., vinyl group, 1-propenyl group and 2-propenyl (allyl) group], and preferably $C_{2-10}$ alkenyl groups.

The cycloalkyl group may include, for example, a $C_{3-15}$ cycloalkyl group (e.g., a cyclopopyl group, a cyclobutyl group, a cyclopentyl group, a cyclohexyl group and a cyclooctyl group), and preferably $C_{3-10}$ cycloalkyl groups.

The aryl group may include, for example, phenyl group, toryl group, naphytyl group, benzyl group, benzhydryl group, cimmnamyl group, cumenyl group, mestyl group, phenylethyl group, phenylene group, styryl group, trityl group and xylyl group.

An ether shown by the formula (2) includes, for example, $diC_{1-15}$alkylethers such as dimethylether, diethylthel, dipropylether, diisopropylether, dibutylether, diisobutylylether, dipentylether, diisopentyl, dihexylether and diheptylether (preferably $diC_{1-10}$alkylethers); $diC_{2-15}$alkenylethers such as diallylether (preferably $diC_{2-10}$alkenylethers); $C_{1-15}$alkyl$C_{1-15}$alkylethers, provided that $R^{7a}$ is different from $R^{7b}$ such as ethylmethylether, 2-methoxypropane, methylbuthylether, 2-methoxybutane, 2-methoxypentane, 1-ethoxypropane, 2-ethoxypropane, 1-ethoxybutane, 2-ethoxybutane, 1-ethxypentane and 2-ethoxypentane (preferably $C_{1-10}$alkyl$C_{1-10}$alkylethers, provided that $R^{7a}$ is different from $R^{7b}$); $C_{2-15}$alkenyl$C_{2-15}$alkenylethers, provided that $R^{7a}$ is different from $R^{7b}$ such as vinylallylether (preferably $C_{2-10}$alkenyl$C_{2-10}$alkenylethers, provided that $R^{7a}$ is different from $R^{7b}$); $C_{1-15}$alkyl$C_{2-15}$alkenylethers such as methylvinylether, methylallylether, ethylallylether, ethoxyethylene and 3-ethoxypropylene (preferably $C_{1-10}$alkyl$C_{2-10}$alkenylethers).

Ethers of the formula (3) include, for example, $C_{1-15}$alkyl$C_{3-15}$cycloalkylethers such as cyclopropylethylether, cyclopropylpropylether, cyclopropylbutylether, cyclobutylethylether, cyclobutylpropylether, cyclobutylbutylether, cyclopentylethylether, cyclopentylpropylether, cyclopentylbutylether, cyclohexylethylether, cyclohexylpropylether and cyclohexylbutylether (preferably $C_{1-10}$alkyl$C_{3-10}$cycloalkylethers; $C_{2-15}$alkenyl$C_{3-15}$cycloalkylethers such as allylcyclohexylether (preferably $C_{2-10}$alkenyl$C_{3-10}$cycloalkylethers); $C_{1-15}$alkylarylethers such as methylphenylether (anisole), ethylphenylether (phenetole), propylphenylether, benzylmethyether, benzylethylether, benzylpropylether, anethole, naphtylmethylether, naphtylethylether and triethylether (preferably $C_{1-10}$alkylarylethers); $C_{2-15}$alkenylarylethers such as allylphenylether (preferably $C_{2-10}$alkenylarylethers).

An ether shown by the formula (2) and (3) includes a polyether having plural ether bonds such as 1,2-dimethoxyethane, diethyleneglycoldimethylether, 3,6-dioxyoctane, p-dimethoxybenzene, p-diethoxybenzene, 1,1'-(ethylenedioxy)dibenzene.

A cyclic ether refers to a compound having an ether bond in a cyclic structure. There is no limit as to an alicyclic ether. The ether ring having an oxygen atom may be a condensed by a ring [such as an aromatic ring (an aryl ring), a heterocyclic ring]. Incidentally, the cyclic ether refers to an ether ring having an oxygen atom which is condensed by an aromatic ring in the specification.

An ether ring of the cyclic ether includes, for example, a cyclic ether having about 3 to 30 members (e.g., 3 to 20 members), preferably about 3 to 16 members, and particularly about 3 to 14 members (e.g., 4 to 10 members).

The cyclic ether includes, for example, heterocyclic ethers such as oxirane, oxetone, propyleneoxide, tetrahydrofuran, tetarhydropyran, oxepane, 2-metyltetrahydrofuran, pyran, 1,3-dihydroxyisobenzofuran, chroman, chromene, isochroman, xanthene, and 5,6-didehydrooxonane; heterocyclic spiro compounds such as 1-oxaspiro[4.5]decane, and tetrahydropyran-2-spirocyclohexane.

The cyclic ether includes a polycyclic ether having a pluar of ether bonds such as dioxane, 1,3,5,7-tetraoxane, 3,6,8-trioxabicyclo[3.2.2]nonane and a crown ether.

A carbon atom of the ether may be substituted with various substituents such as a halogen atom (e.g., iodine, bromine, chloride and fluorine), an oxo group, a hydroxyl group, a hydroxyalkyl group (e.g., hydroxymethyl, 2-hydroxyethyl and other hydroxy$C_{1-4}$alkyl group), a carboxyl group, an alkoxycarbonyl group (e.g., methoxycarbonyl, ethoxycarbonyl, propoxycarbonyl, isopropoxycarbonyl, butoxycarbonyl, isobutoxycarbonyl, t-butoxycarbonyl, hexyloxycarbonyl group and other lower alkoxycarbonyl groups having about 1 to 6 carbon atoms in an alkoxy moiety (particularly about 1 to 4 carbon atoms), an amino group, a substituted amino group, a cyano group, and a nitro group. In particular, a carbon atom adjacent to an ether bond may be substituted with an oxo group.

An ether having a substituent at a carbon atom therein includes, for example, an ether having a halogen atom [e.g., 1-chloro-2-ethoxyethane, bis(2-chloroethyl)ether], an ether having an oxo group (e.g., phthalide), an ether having a hydroxyl group (e.g., 2-methoxyethanol, 2-ethoxyethanol, 2,2'-oxydiethanol, 3,6-dioxooctane-1,8-diol, 2-methoxyphenol, eugenol), an ether having an carboxyl group [e.g., 3.3'-oxydipropionic acid, 4,4'-(ethylenedioxy) dibenzoic acid].

When such ethers are oxidized by the oxidation process of the present invention, the carbon site adjacent to the oxygen atom of the ether bond is oxidized even in mild or moderate condition to produce the corresponding chain or cyclic ester, carboxylic acid or acid anhydride efficiently.

In particular, use of a cyclic ether easily to form a lactone (e.g., β-propiolactone, γ-butylolactone, δ-valerolactone, ε-caprolactam) or an anhydride (e.g., succinic anhydride, glutaric anhydride) corresponding to the cyclic ether (i.e., the number of member in the ether ring.

Incidentally, the carbon site which is not adjacent to the oxygen atom of the ether bond may sometimes be oxidized depending on the species of ethers. For example, in the case of xanthene, an adjacent site to an aromatic ring thereof may be sometimes oxidized to produce a ketone.

In another case of a chain ether, a carbon site adjacent to an oxygen atom is mainly oxidized, but depending on reaction conditions, the ether is cut to produce the corresponding carboxylic acid or alcohol as the reaction proceeds.

Therefore, the oxidation process of ethers of the present invention is also useful for producing a ketone body or a carboxylic acid.

Oxidation Reaction

The oxygen used in oxidation of an ether may be active oxygen, but molecular oxygen is practically employed for economical advantages. Such molecular oxygen is not specifically limited, and use may be made of whichever of pure oxygen, or oxygen diluted with an inert gas such as nitrogen, helium, argon or carbon dioxide gas. Air is preferably employed from the viewpoints of not only handling property and safety, but also economical prop- erty.

The amount of oxygen may be selected from a range according to the variety of the substrate, and usually is, about 0.5 mole or more (e.g., about 1 mole or more), preferably about 1 to 100 mole, and more preferably about 2 to 50 mole relative to 1 mole of the substrate. The oxygen is practically used in an excess mole relative to the substrate. In specific, the reaction is advantageously carried out in an atmosphere containing molecular oxygen such as air or oxygen gas.

Oxidation process of the present invention is usually conducted in an organic solvent inert to the reaction. As the organic solvents, there may be mentioned, for example, acetic acid, propionic acid and other organic acids, acetonitrile, propionitrile, benzonitrile and other nitrites, formamide, acetamide, dimethylformamide (DMF), dimethylacetamide and other amides, hexane, octane and other aliphatic hydrocarbons, benzene, toluene and other aromatic hydrocarbons, chloroform, dichloromethane, dichloroethane, carbon tetrachloride, chlorobenzene and other halogenated hydrocarbons, nitrobenzene, nitromethane, nitroethane and other nitro compounds, ethyl acetate, butyl acetate and other esters, or mixtures of these solvents. Incidentally, the substrate may be employed as the reaction solvent, if used in an excess amount. Use may practically be made of, as the solvent, acetic acid or other organic acids, acetonitrile or other nitrites.

The process of the present invention is characterized in that the oxidation reaction smoothly proceeds even in comparatively mild or moderate conditions. A reaction temperature can be voluntarily selected according to the species of the substrate and so forth. The temperature is, for instance, about 0 to 300° C., preferably about 30 to 250° C., more preferably about 40 to 200° C., and practically about 50 to 150° C. The reaction may be carried out at ambient pressure (atmospheric pressure) or under a pressure (under a load). When the reaction is conducted under a pressure, the pressure is, usually, about 1 to 100 atm (e.g., about 1.5 to 80 atm), preferably about 2 to 70 atm, and more preferably about 5 to 50 atm. A reaction time can be liberally chosen within a range of about 30 minutes to 48 hours, preferably about 1 to 36 hours, and more preferably about 2 to 24 hours, according to the reaction temperature and pressure.

The reaction may be effected merely by contacting a substrate with oxygen in the presence of the above catalyst, or in a conventional manner such as in a batch system, semi-batch system or continuous system, in the presence of molecular oxygen or under flow of molecular oxygen. After completion of the reaction, a reaction product can easily be isolated and purified according to a conventional technology, such as filtration, condensation, distillation, extraction, crystallization, recrystallization, column chromatography, or other isolation means, or a combination of these technologies.

INDUSTRIAL APPLICABILITY OF THE INVENTION

In the process of the present invention, an ester and an acid anhydride may be obtained from an ether. They are useful for an intermediate of a medicine, a perfume, a dye and a food, an intermediate in organic synthesis, and an intermediate compound of a raw material of polymer resin. It is easy to produce a dicarboxylic acid by hydration of an acid anhydride.

In the oxidation process of the present invention, an ether may be efficiently oxidized by oxidizing with oxygen as the oxidation catalyst comprising (i) an imide compound shown by the formula (1) or (ii) the imide compound and a co-catalyst is used. Even in a mild or moderate condition, an ether may be efficiently oxidized with oxygen. Therefore, the process is useful for producing an oxide of an ether (such as a chain or cyclic ester, an acid anhydride) with high conversion and selectivity.

EXAMPLES

The following examples are intended to describe this invention in further detail and should by no means be interpreted as defining the scope of the invention.

Example 1

A mixture of 3 mmole of tetrahydropyran, 10 mole % of N-hydroxyphthalimide relative to tetrahydropyran, 0.5 mole % of acetylacetonatocobalt(II) Co(AA)$_2$ relative to tetrahydropyran, and 5 ml of acetonitrile was stirred for 6 hours at 60° C. under an oxygen atmosphere. The products in the reaction mixture were analyzed by gas chromarography, and, as a result, tetrahydropyran was converted into δ-valerolactone (yield 22%), glutaric acid (yield 6%) and glutaric anhydride (yield 6%) with a conversion of 40%.

Example 2

The reaction was conducted in the same manner as Example 1 except for using acetic acid instead of acetonitrile, and, as a result, tetrahydropyran was converted into δ-valerolactone (yield 26%), glutaric acid (yield 10%) and glutaric anhydride (yield 14%) with a conversion of 62%.

Example 3

A mixture of 3 mmole of tetrahydropyran, 10 mole % of N-hydroxyphthalimide relative to tetrahydropyran, 0.5 mole % of acetylacetonatocobalt(II) Co(AA)$_2$ relative to tetrahydropyran, and 5 ml of acetic acid was stirred for 15 hours at 60° C. under an oxygen atmosphere. The products in the reaction mixture were analyzed by gas chromarography, and, as a result, tetrahydropyran was converted into δ-valerolactone (yield 28%), glutaric acid (yield 11%) and glutaric anhydride (yield 9%) with a conversion of 67%.

Example 4

A mixture of 3 mmole of oxepane, 10 mole % of N-hydroxyphthalimide relative to oxepane, 0.5 mole % of acetylacetonatocobalt(II) Co(AA)$_2$ relative to oxepane, and 5 ml of acetonitrile was stirred for 8 hours at 60° C. under an oxygen atmosphere. The products in the reaction mixture were analyzed by gas chromarography, and, as a result, oxepane was converted into ε-caprolactam (yield 28%), adipic acid (yield 10%) and adipic anhydride (yield 8%) with a conversion of 74%.

Example 5

A mixture of 2 mmole of isochroman, 3 mole % of N-hydroxyphthalimide relative to isochroman, 0.5 mole % of acetylacetonatocobalt(II) Co(AA)$_2$ relative to isochroman, and 5 ml of benzonitrile was stirred for 8 hours at 85° C. under an oxygen atmosphere. The products in the reaction mixture were analyzed by gas chromatography, and, as a result, isocoumalin (yield 99%) were formed.

Example 6

A mixture of 2 mmole of benzylmethylether, 2 mole % of N-hydroxyphthalimide relative to benzylmethylether, and 5 ml of benzonitrile was stirred for 12 hours at 100° C. under an oxygen atmosphere. The products in the reaction mixture were analyzed by gas chromarography, and, as a result, methyl benzoate (yield 60%) was formed.

Example 7

A mixture of 2 mmole of diheptylether, 3 mole % of N-hydroxyphthalimide relative to diheptylether, and 5 ml of benzonitrile was stirred for 20 hours at 100° C. under an oxygen atmosphere. The products in the reaction mixture were analyzed by gas chromarography, and, as a result, hexyl heptylate (yield 16%) was formed.

Example 8

A mixture of 2 mmole of xanthene, 10 mole % of N-hydroxyphthalimide relative to xanthene, and 5 ml of benzonitrile was stirred for 20 hours at 100° C. under an oxygen atmosphere. The products in the reaction mixture were analyzed by gas chromatography, and, as a result, 9-oxoxanthene (yield not less than 99%) was formed.

Example 9

A mixture of 2 mmole of phthalide, 2 mole % of N-hydroxyphthalimide relative to phthalide, and 5 ml of benzonitrile was stirred for 12 hours at 100° C. under an oxygen atmosphere. The products in the reaction mixture were analyzed by gas chromarography, and, as a result, phthalic anhydride (yield 46%) was formed.

Obvious from the above Examples, ethers may be well oxidized to produce the corresponding oxides (such as esters, acid anhydrides, carboxylic acids, alcohols) efficiently. A carbon site which is not adjacent to an oxygen atom of an ether bond or a cyclic ester may be oxidized.

What is claimed is:

1. An oxidation process of an ether, which comprises contacting an ether with oxygen in the presence of an oxidation catalyst comprising an imide compound shown by the following formula (1):

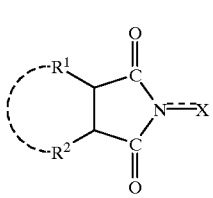

(1)

wherein $R^1$ and $R^2$ independently represent a hydrogen atom, a halogen atom, an alkyl group, an aryl group, a cycloalkyl group, a hydroxyl group, an alkoxy group, a carboxyl group, an alkoxycarbonyl group, or an acyl group, or $R^1$ and $R^2$ may bond together to form a double bond or an aromatic or non-aromatic ring, and the aromatic or non-aromatic ring formed by $R^1$ and $R^2$ may have 1 or 2 of an imide unit shown by the following formula:

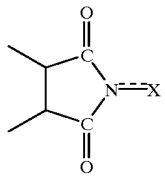

X represents an oxygen atom or a hydroxyl group, and a co-catalyst containing at least one element selected from the group consisting of Group 2A elements of the Periodic Table of Elements, transition metal elements and Group 3B elements of the Periodic Table of Elements, with a proviso that said co-catalyst is other than vanadomolybdophosphate.

2. An oxidation process according to claim 1, wherein $R^1$ and $R^2$, in said imide compound shown by the formula (1), bond together to form an aromatic or a non-aromatic 5 to 12 membered ring.

3. An oxidation process according to claim 1, wherein $R^1$ and $R^2$, in said imide compound shown by the formula (1), bond together to form a cycloalkane ring which may have a substituent, a cycloalkene ring which may have a substituent, a bridged hydrocarbon ring which may have a substituent and an aromatic ring which may have a substituent.

4. An oxidation process according to claim 1, wherein said imide compound shown by the formula (1) is a compound formulas (1a), (1b), (1c), (1d), (1e) and (1f):

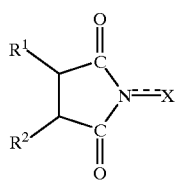
(1a)

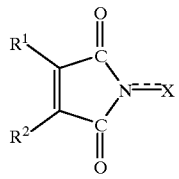
(1b)

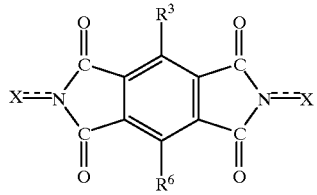
(1c)

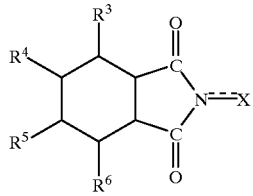
(1d)

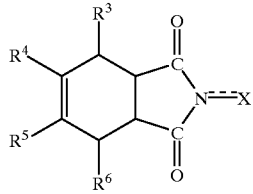
(1e)

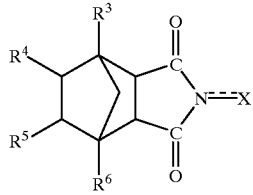
(1f)

wherein $R^3$, $R^4$, $R^5$ and $R^6$ are the same or different, a hydrogen atom, an alkyl group, a hydroxyl group, an alkoxy group, a carboxyl group, an alkoxycarbonyl group, an acyl group, a nitro group, a cyano group, an amino group or a halogen atom; and $R^1$, $R^2$ and X have the same meanings as defined above.

5. An oxidation process according to claim 1, wherein said imide compound shown by the formula (1) is at least one compound selected from the group consisting of N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide, N-hydroxytrimellitimide, N,N'-dihydroxypyromellitimide and N,N'-dihydroxynaphthalenetetracarboximide.

6. An oxidation process according claim 1, wherein the co-catalyst comprises a transition metal.

7. An oxidation process according to claim 1, wherein said co-catalyst is a compound containing at least one element selected from the group consisting of Group 3A elements, Group 4A elements, Group 5A elements, Group 6A elements, Group 7A elements, Group 8 elements, Group 1B elements and Group 2B elements of the Periodic Table of Elements.

8. An oxidation process according to claim 1, wherein the ether is a cyclic ether having 3 to 30 members.

9. A process for producing an ester or an anhydride which comprises contacting an ether with oxygen in the presence of the oxidation catalyst according to claim 1 or 2.

10. An oxidation process according to claim 1, wherein a relative ratio of the co-catalyst to 1 mole of the ether is 0.0001 to 1 moles.

* * * * *